US010982351B2

(12) United States Patent
Jung

(10) Patent No.: US 10,982,351 B2
(45) Date of Patent: Apr. 20, 2021

(54) METHODS FOR HIGH EFFICIENCY LIBRARY PREPARATION USING DOUBLE-STRANDED ADAPTERS

(71) Applicant: GRAIL, Inc., Menlo Park, CA (US)

(72) Inventor: Byoungsok Jung, Atherton, CA (US)

(73) Assignee: GRAIL, Inc., Menlo Park, CA (US)

( * ) Notice: Subject to any disclaimer, the term of this patent is extended or adjusted under 35 U.S.C. 154(b) by 556 days.

(21) Appl. No.: 15/853,200

(22) Filed: Dec. 22, 2017

(65) Prior Publication Data

US 2018/0216252 A1    Aug. 2, 2018

Related U.S. Application Data

(60) Provisional application No. 62/438,911, filed on Dec. 23, 2016.

(51) Int. Cl.
| | | |
|---|---|---|
| *C12Q 1/68* | (2018.01) | |
| *C40B 20/04* | (2006.01) | |
| *C40B 40/06* | (2006.01) | |
| *C40B 50/04* | (2006.01) | |
| *C40B 50/06* | (2006.01) | |
| *C12Q 1/6869* | (2018.01) | |
| *C12Q 1/6806* | (2018.01) | |
| *C12Q 1/6855* | (2018.01) | |

(52) U.S. Cl.
CPC ............ *C40B 40/06* (2013.01); *C12Q 1/6806* (2013.01); *C12Q 1/6855* (2013.01); *C12Q 1/6869* (2013.01); *C40B 20/04* (2013.01); *C40B 50/04* (2013.01); *C40B 50/06* (2013.01)

(58) Field of Classification Search
CPC .. C12Q 1/6806; C12Q 1/6855; C12Q 1/6869; C12Q 2525/191; C12Q 2537/1376; C40B 20/04; C40B 40/06; C40B 50/06
See application file for complete search history.

(56) References Cited

U.S. PATENT DOCUMENTS

| | | | |
|---|---|---|---|
| 4,683,195 A | 7/1987 | Mullis et al. | |
| 6,818,395 B1 | 11/2004 | Quake et al. | |
| 7,169,560 B2 | 1/2007 | Lapidus et al. | |
| 7,282,337 B1 | 10/2007 | Harris | |
| 7,297,518 B2 | 11/2007 | Quake et al. | |
| 7,666,593 B2 | 2/2010 | Lapidus | |
| 7,897,345 B2 | 3/2011 | Lapidus et al. | |
| 7,948,015 B2 | 5/2011 | Rothberg et al. | |
| 8,262,900 B2 | 9/2012 | Rothberg et al. | |
| 8,306,757 B2 | 11/2012 | Rothberg et al. | |
| 8,349,167 B2 | 1/2013 | Rothberg et al. | |
| 8,426,898 B2 | 4/2013 | Rothberg et al. | |
| 8,546,128 B2 | 10/2013 | Schultz et al. | |
| 8,574,835 B2 | 11/2013 | Hinz et al. | |
| 8,673,627 B2 | 3/2014 | Nobile et al. | |
| 2002/0164629 A1 | 11/2002 | Quake et al. | |
| 2009/0026082 A1 | 1/2009 | Rothberg et al. | |
| 2009/0127589 A1 | 5/2009 | Rothberg et al. | |
| 2009/0156412 A1 | 6/2009 | Harris et al. | |
| 2009/0191565 A1 | 7/2009 | Lapidus et al. | |
| 2010/0035252 A1 | 2/2010 | Rothberg et al. | |
| 2010/0137143 A1 | 6/2010 | Rothberg et al. | |
| 2010/0167954 A1 | 7/2010 | Earnshaw et al. | |
| 2010/0188073 A1 | 7/2010 | Rothberg et al. | |
| 2010/0197507 A1 | 8/2010 | Rothberg et al. | |
| 2010/0282617 A1 | 11/2010 | Rothberg et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2010/0304982 A1 | 12/2010 | Hinz et al. | |
| 2013/0116130 A1* | 5/2013 | Fu ....................... | C12Q 1/6809 506/4 |
| 2015/0197798 A1 | 7/2015 | Xu et al. | |
| 2015/0299767 A1* | 10/2015 | Armour ............. | C12N 15/1093 506/9 |
| 2015/0376608 A1 | 12/2015 | Kaper et al. | |
| 2016/0017412 A1 | 1/2016 | Srinivasan et al. | |
| 2016/0304947 A1 | 10/2016 | Hajeri et al. | |
| 2016/0319345 A1 | 11/2016 | Gnerre et al. | |
| 2016/0333416 A1 | 11/2016 | Babiarz et al. | |
| 2017/0016048 A1 | 1/2017 | Blauwkamp et al. | |

(Continued)

FOREIGN PATENT DOCUMENTS

| | | |
|---|---|---|
| WO | 99/04041 | 1/1999 |
| WO | 2007/052006 | 5/2007 |
| WO | 2009/072972 | 6/2009 |

(Continued)

OTHER PUBLICATIONS

Turchinovich et al., "Capture and Amplification by Tailing and Switching (CATS). An Ultrasensitive Ligation-independent Method for Generation of DNA Libraries for Deep Sequencing from RNA Biology," RNA Biology, Landes Bioscience, US, Vo. 11, No. 7, Jul. 2014, pp. 817-828.

Kennedy et al, "Detecting Ultralow-frequency Mutations by Duplex-sequencing," Nature Protocols, vol. 9, No. 11, Oct. 2014, pp. 2586-2606.

Head et al., "Library Construction for Next-generation Sequencing: Overviews and Challenges," BioTechniques, Jan. 2014, pp. 61-77.

Duncavage et al., "Hybrid Capture and Next-generation Sequencing Identify Viral Integration Sites from Formalin-fixed, Paraffin-embedded Tissue," J Mol Diagn. vol. 13, No. 3, May 2011, pp. 325-333.

(Continued)

*Primary Examiner* — David C Thomas
(74) *Attorney, Agent, or Firm* — Benjamin C. Pelletier; Haynes and Boone LLP

(57) ABSTRACT

Methods for preparing a sequencing library from a DNA-containing test sample are provided, including methods for rescuing one or more partially ligated DNA fragments to enhance library preparation conversion efficiencies. The subject methods can further be used to improve recovery of duplex sequence information from double-stranded DNA.

17 Claims, 4 Drawing Sheets

(56) References Cited

U.S. PATENT DOCUMENTS

2017/0044525 A1 2/2017 Kaper et al.
2017/0327882 A1 11/2017 Betts et al.

FOREIGN PATENT DOCUMENTS

| WO | 2009/109753 | | 9/2009 |
|---|---|---|---|
| WO | 2009/133466 | | 11/2009 |
| WO | 2013/142389 | | 9/2013 |
| WO | 2014/008447 | | 1/2014 |
| WO | 2014/066179 | | 5/2014 |
| WO | 2015/057319 | | 4/2015 |
| WO | 2015/094861 | | 6/2015 |
| WO | 2015/117040 | | 8/2015 |
| WO | 2015/122967 | | 8/2015 |
| WO | 2015/134552 | A1 | 9/2015 |
| WO | 2015/168161 | | 11/2015 |
| WO | 2015/200609 | | 12/2015 |
| WO | 2016/034433 | | 3/2016 |
| WO | 2016/170147 | | 10/2016 |
| WO | 2016/172373 | | 10/2016 |
| WO | 2016/176091 | | 11/2016 |
| WO | 2017/040306 | | 3/2017 |
| WO | 2017/044574 | | 3/2017 |
| WO | 2017/218512 | | 12/2017 |
| WO | 2018/031929 | | 2/2018 |

OTHER PUBLICATIONS

Newman et al., "An Ultrasensitive Method for Quantitating Circulating Tumor DNA with Broad Patient Coverage," Nat Med. vol. 20, No. 5, May 2014, pp. 548-554.
Harris et al., "Single-molecule DNA Sequencing of a Viral Genome," Science, vol. 320, No. 5872, Apr. 2008, pp. 106-109.
Braslaysky et al., "Sequence Information can be Obtained from Single DNA Molecules," PNAS, vol. 100, No. 7, Apr. 2003, pp. 3960-3964.
Margulies et al., "Genome Sequencing in Microfabricated Highdensity Picolitre Reactors," Nature, vol. 437, Sep. 2005, pp. 376-380.
Soni and Meller, "Progress Toward Ultrafast DNA Sequencing Using Solid-state Nanopores," Clin Chem vol. 53, No. 11, 2007, pp. 1996-2001.
Mouliere and Rosenfeld, "Circulating Tumor-derived DNA is Shorter than Somatic DNA in Plasma," PNAS, vol. 112, No. 11, Mar. 2015, pp. 3178-3179.
Jiang et al., "Lengthening and Shortening of Plasma DNA in Hepatocellular Carcinoma in Patients," PNAS, vol. 112, No. 11, Feb. 2015, pp. E1317-E1325.
Mouliere et al. "Multi-marker Analysis of Circulating Cell-free DNA Toward Personalized Medicine for Colorectal Cancer," Mol Oncol. vol. 8, No. 5, Mar. 2014, pp. 927-947.
Bettegowda et al., "Detection of Circulating Tumor DNA in Early- and Late-stage Human Malignancies," Sci Trans Med, vol. 6, No. 224, Feb. 2014, 224ra24.
Bodi et al., "Comparison of Commercially Available Target Enrichment Methods for Next-Generation Sequencing," (2013) J. Biomol Tech., 24(2):73-86.
Latorra et al., "Design Considerations and Effects of LNA in PCR Primers," (2003) Molecular and Celular Probes 17:253-259.
Levin et al., "Position-dependent Effects of Locked Nulceic Acid (LNA) on DNA Sequencing and PCR Primers," (2006) Nucleic Acids Research, 34(20):e152.
International Search Report and Written Opinion, PCT Application No. PCT/US2017/068196, dated Mar. 2, 2018.
International Search Report and Written Opinion, PCT Application No. PCT/US2018/025475, dated Aug. 10, 2018.
Cheng et al., "Memorial Sloan Kettering-Integrated Mutation Profiling of Actionable Cancer Targets (MSK-IMPACT)," (2015) Journal of Molecular Diagnostics 17(3):251-264.
Johannsen et al., "Enzymatic polymerisation involving 2-amino-LNA nucleotides," (2012) Bioorganic & Medicinal Chemistry Letters, 22 (10):3522-3526.
Kuwahara et al., "Study on Suitability of KOD DNA Polymerase for Enzymatic Production of Artificial Nucleic Acids Using Base/Sugar Modified Nucleoside Triphosphates," (2010) Molecules, 15(11):8229-8240.
Maxam et al., "A new method for sequencing DNA," (1997) PNAS 74(2):560-564.
Moudrianakis et al., "Base Sequence Determination in Nucleic Acids With the Electron Microscope III. chemistry and microscopy of guanine-labeled DNA," (1965) PNAS 53(3):564-671.
Nagalakshmi et al., "RNA-Seq: A Method for Comprehensive Transcriptome Analysis,". (2010) Current Protocols in Molecular Biology.
Nguyen, "Design of modified A*U and G*C base pairs with similar stability, implication for teh DNA sequencing by hybridization," (1997) Tetrahedron Letters 38(43):7515-7518.
Nguyen et al., "Modification of DNA duplexes to smooth their thermal stability independently of their base content for DNA sequencing by hybridization," (1997) NAR 25(15):3059-3065.
Nguyen et al., "Smoothing of the thermal stability of DNA duplexes by using modified nucleosides and chaotropic agents," (1999) NAR 27(6):1492-1498.
Nguyen et al., "Studies towards the design of a modified GC base pair with stability similar to that of the at base pair," (1997) Tetrahedron Letters 38(23):4082-4086.
Nguyen et al. "The stability of duplexes involving AT and/or G4Etc base pairs is not dependent on their AT/G4EtC ratio content. Implication for DNA sequencing by hybridization" (1998) NAR,26(18):4249-4258.
Sanger et al., "DNA sequencing with chain-terminating inhibitors," (1997) PNAS 74(12):5463-5467.
Veedu et al., "In vitro incorporation of LNA nucleotides," (2007) Nucleosides, Nucleotides and Nucleic Acids 26 (8-9):1207-1210.
Veedu et al., "Locked nucleic acid nucleoside triphosphates and polymerases: on the way towards evolution of LNA aptamers," (2009) Molecular Biosystems 5(8):787-792.
Veedu et al., "Locked Nucleic Acids Promising Nucleic Acid Analogs for Therapeutic Applications," (2010) Chemistry & Biodiversity 7(3):536-542.
Veedu et al. , "Polymerase chain reaction and transcription using locked nucleic acid nucleotide triphosphates" (2008) Journal of the American Chemical Society 130(26):8124-8125.
Veedu et al., "Polymerase directed incorporation studies of LNA-G nucleoside 5'—triphosphate and primer extension involving all four LNA nucleotides," (2010) New Journal of Chemistry, 34(5):877.
Veedu et al., "Polymerase-directed synthesis of C5-ethynyl locked nucleic acids," (2010) Bioorganic & Medicinal Chemistry Letters 20(22):6565-6568.

\* cited by examiner

METHODS FOR HIGH EFFICIENCY LIBRARY PREPARATION USING DOUBLE-STRANDED ADAPTERS

CROSS REFERENCE TO RELATED APPLICATIONS

Under 35 U.S.C. § 119(e), this application claims priority benefit of the filing date of U.S. Provisional Patent Application Ser. No. 62/438,911, filed on Dec. 23, 2016, the disclosure of which application is herein incorporated by reference in its entirety.

FIELD OF THE INVENTION

The present invention relates to molecular biology techniques and methods for preparing sequencing libraries from DNA-containing test samples.

BACKGROUND OF THE INVENTION

Analysis of circulating cell-free nucleic acids (e.g., cell-free DNA (cfDNA)) using next generation sequencing (NGS) is recognized as a valuable diagnostic tool for many diseases. Identifying rare variants indicative of cancer using NGS often requires deep sequencing of circulating cfDNA from a patient test sample. Alternatively, many tumor-derived variants can also be identified using less expensive lower depth, whole exome sequencing approaches. However, errors introduced during sample preparation and sequencing can make accurate identification of variants difficult.

Duplexed sequence reads are critical for error correction in sequencing applications that typically use low input levels of material and/or have limited sequencing coverage (e.g., analysis of cfDNA). For error correction, particularly in limited depth exome sequencing, it is important to avoid sequencing non-duplex DNA molecules. Current protocols for preparing a sequencing library from double-stranded DNA typically includes DNA end repair, 3' end A-tailing, ligation of sequencing adapters to the double-stranded (duplexed) DNA, and polymerase chain reaction (PCR) amplification to enrich for adapter ligated DNA molecules. The procedure requires four successful ligation events to obtain sequenceable fragments for both the forward and reverse strands of a double-stranded DNA molecule. If a single ligation event fails during library preparation, one strand of the duplexed library fragment will not be amplified and a non-duplexed read will be observed during sequence analysis. However, as one of skill in the art would readily recognize, these individual ligation events are not 100% efficient, and sequence information from the test sample can be lost. Accordingly, there is a need in the art for new methods of preparing sequencing libraries that enrich for duplexed DNA molecules, thereby increasing duplex reads in sequencing.

SUMMARY OF THE INVENTION

Aspects of the invention include methods for preparing a sequencing library from a DNA-containing test sample. In one aspect, the present invention is directed to methods for rescuing one or more partially ligated DNA fragments to enhance library preparation conversion efficiencies. In other aspects, the methods can be used to improve recovery of duplex sequence information from double-stranded DNA.

In one embodiment, the present invention is directed to a method for preparing a double-stranded DNA sequencing library, the method comprising the following steps: (a) obtaining a test sample comprising a plurality of double-stranded DNA (dsDNA) fragments, wherein the dsDNA fragments comprise a forward strand and a reverse strand; (b) ligating double-strand DNA adapters to both ends of the dsDNA fragments; and (c) extending unligated 3'-ends of the dsDNA fragments with a DNA polymerase to create dsDNA fragment-adapter templates to prepare a sequencing library. In some embodiments, the dsDNA fragment-adapter templates are further amplified prior to sequencing. In other embodiments, one or more steps of the method may be carried out in a single reaction step. For example, steps (b) through (c) may be carried out in a single reaction tube utilizing a reaction mixture comprising a first set of dsDNA adapters, a ligase, a polymerase (optionally having strand-displacement activity), a terminal deoxynucleotidyl transferase, and a second set of ssDNA oligonucleotides or primers (e.g., including sequencing adapters and/or a universal primer). Optionally, the dsDNA molecules can be purified, and optionally fragmented, from test sample prior to ligation step (b).

In another embodiment, the present invention is directed to a method for preparing a double-stranded DNA sequencing library, the method comprising the following steps: (a) obtaining a test sample comprising a plurality of double-stranded DNA (dsDNA) fragments, the dsDNA fragments comprising a forward strand and a reverse strand; (b) adding double-stranded adapters to the dsDNA fragments and ligating the double-strand adapters to both ends of the dsDNA fragments; (c) extending unligated 3'-ends of the dsDNA fragments with a DNA polymerase to create dsDNA fragment-adapter templates, wherein the polymerase further comprises strand displacement activity; (d) adding a polyadenine tail to the 3'-ends of the dsDNA fragment-adapter templates; (e) adding a set of ssDNA oligonucleotides (or primers) and hybridizing the ssDNA oligonucleotides to the dsDNA fragment-adapter templates; and (f) extending the set of ssDNA oligonucleotides to create a dsDNA sequencing library. In some embodiments, one or more steps of the method may be carried out in a single reaction step. For example, steps (b) through (f) may be carried out in a single reaction tube utilizing a reaction mixture comprising a first set of dsDNA adapters, a ligase, a polymerase (optionally having strand-displacement activity), a terminal deoxynucleotidyl transferase, and a second set of ssDNA oligonucleotides or primers (e.g., including sequencing adapters and/or a universal primer). Optionally, the dsDNA molecules can be purified, and optionally fragmented, from test sample prior to ligation step (b).

DEFINITIONS

Figure 1:
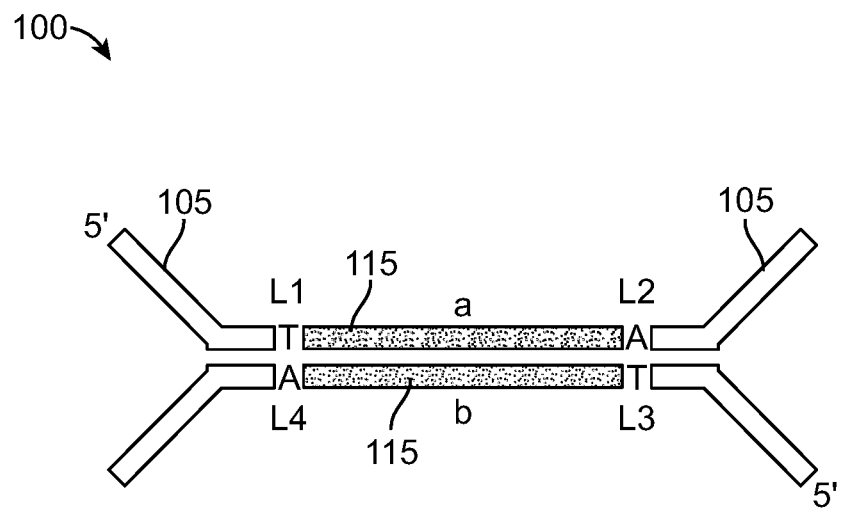
FIG. 1 is a schematic illustration showing the four ligation steps (L1, L2, L3 and L4) that must occur in conventional dsDNA library preparation methods to obtain sequenceable dsDNA molecules.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application, as do the following, each of which is incorporated by reference herein in its entirety: Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, 6*th* edition (Saunders, 2007).

All publications mentioned herein are expressly incorporated herein by reference to disclose and describe the methods and/or materials in connection with which the publications are cited.

The term "amplicon" as used herein means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase, or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references, each of which are incorporated herein by reference herein in their entirety: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g., "real-time PCR", or "real-time NASBA" as described in Leone et al, Nucleic Acids Research, 26: 2150-2155 (1998), and like references.

As used herein, the term "amplifying" means performing an amplification reaction. A "reaction mixture" means a solution containing all the necessary reactants for performing a reaction, which may include, but is not be limited to, buffering agents to maintain pH at a selected level during a reaction, salts, co-factors, scavengers, and the like.

The terms "fragment" or "segment", as used interchangeably herein, refer to a portion of a larger polynucleotide molecule. A polynucleotide, for example, can be broken up, or fragmented into, a plurality of segments, either through natural processes, as is the case with, e.g., cfDNA fragments that can naturally occur within a biological sample, or through in vitro manipulation. Various methods of fragmenting nucleic acids are well known in the art. These methods may be, for example, either chemical or physical or enzymatic in nature. Enzymatic fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave a polynucleotide at known or unknown locations. Physical fragmentation methods may involve subjecting a polynucleotide to a high shear rate. High shear rates may be produced, for example, by moving DNA through a chamber or channel with pits or spikes, or forcing a DNA sample through a restricted size flow passage, e.g., an aperture having a cross sectional dimension in the micron or submicron range. Other physical methods include sonication and nebulization. Combinations of physical and chemical fragmentation methods may likewise be employed, such as fragmentation by heat and ion-mediated hydrolysis. See, e.g., Sambrook et al., "Molecular Cloning: A Laboratory Manual," 3rd Ed. Cold Spring Harbor Laboratory Press, Cold Spring Harbor, N.Y. (2001) ("Sambrook et al.") which is incorporated herein by reference for all purposes. These methods can be optimized to digest a nucleic acid into fragments of a selected size range.

The terms "polymerase chain reaction" or "PCR", as used interchangeably herein, mean a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors that are well-known to those of ordinary skill in the art, e.g., exemplified by the following references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including, but not limited to, RT-PCR, real-time PCR, nested PCR, quantitative PCR, multiplexed PCR, and the like. The particular format of PCR being employed is discernible by one skilled in the art from the context of an application. Reaction volumes can range from a few hundred nanoliters, e.g., 200 nL, to a few hundred µL, e.g., 200 µL. "Reverse transcription PCR," or "RT-PCR," means a PCR that is preceded by a reverse transcription reaction that converts a target RNA to a complementary single stranded DNA, which is then amplified, an example of which is described in Tecott et al, U.S. Pat. No. 5,168,038, the disclosure of which is incorporated herein by reference in its entirety. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); the disclosures of which are hereby incorporated by reference herein in their entireties. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Asymmetric PCR" means a PCR wherein one of the two primers employed is in great excess concentration so that the reaction is primarily a linear amplification in which one of the two strands of a target nucleic acid is preferentially copied. The excess concentration of asymmetric PCR primers may be expressed as a concentration ratio. Typical ratios are in the range of from 10 to 100. "Multiplexed PCR" means a PCR wherein multiple target sequences (or a single target sequence and one or more reference sequences) are simultaneously carried out in the same reaction mixture, e.g., Bernard et al, Anal. Biochem., 273: 221-228 (1999)(two-color real-time PCR). Usually, distinct sets of primers are employed for each sequence being amplified. Typically, the number of target sequences in a multiplex PCR is in the range of from 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references, which are incorporated by reference herein in their entireties: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); and Becker-Andre et al, Nucleic Acids Research, 17: 9437-9446 (1989).

The term "primer" as used herein means an oligonucleotide, either natural or synthetic, that is capable, upon forming a duplex with a polynucleotide template, of acting as a point of initiation of nucleic acid synthesis and being extended from its 3'-end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually, primers are extended by a DNA polymerase. Primers usually have a length in the range of from 10 to 100 nucleotides, or in the range of from 15 to 60 nucleotides. Primers are employed in a variety of nucleic acid amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following reference that is incorporated by reference herein in its entirety: Dieffenbach, editor, PCR Primer: A Laboratory Manual, $2^{nd}$ Edition (Cold Spring Harbor Press, New York, 2003).

The terms "sequence tag", "tag" or "barcode", as used interchangeably herein, refer to an oligonucleotide that is attached to a polynucleotide or template molecule and is used to identify and/or track the polynucleotide or template in a reaction or a series of reactions. A sequence tag may be unique to a given molecule in a sample (e.g., unique molecular identifiers (UMIs)) and used to track amplicons derived therefrom (e.g., through PCR amplification), or specific to a test sample (i.e., a sample-specific sequence tag) and used for multiplexing in sequencing. A sequence tag may be attached to the 3'- or 5'-end of a polynucleotide or template, or it may be inserted into the interior of such polynucleotide or template to form a linear conjugate, sometimes referred to herein as a "tagged polynucleotide," or "tagged template," or the like. Sequence tags may vary widely in size and compositions; the following references, which are incorporated herein by reference in their entireties, provide guidance for selecting sets of sequence tags appropriate for particular embodiments: Brenner, U.S. Pat. No. 5,635,400; Brenner and Macevicz, U.S. Pat. No. 7,537, 897; Brenner et al, Proc. Natl. Acad. Sci., 97: 1665-1670 (2000); Church et al, European patent publication 0 303 459; Shoemaker et al, Nature Genetics, 14: 450-456 (1996); Morris et al, European patent publication 0799897A1; Wallace, U.S. Pat. No. 5,981,179; and the like. Lengths and compositions of sequence tags can vary widely, and the selection of particular lengths and/or compositions depends on several factors including, without limitation, how tags are used to generate a readout, e.g., via a hybridization reaction or via an enzymatic reaction, such as sequencing; whether they are labeled, e.g., with a fluorescent dye or the like; the number of distinguishable oligonucleotide tags required to unambiguously identify a set of polynucleotides, and the like, and how different the tags of a particular set must be in order to ensure reliable identification, e.g., freedom from cross hybridization or misidentification from sequencing errors. In one aspect, sequence tags can each have a length within a range of from about 2 to about 36 nucleotides, or from about 4 to about 30 nucleotides, or from about 4 to about 20 nucleotides, or from about 8 to about 20 nucleotides, or from about 6 to about 10 nucleotides. In one aspect, sets of sequence tags are used, wherein each sequence tag of a set has a unique nucleotide sequence that differs from that of every other tag of the same set by at least two bases; in another aspect, sets of sequence tags are used wherein the sequence of each tag of a set differs from that of every other tag of the same set by at least three bases.

The terms "subject" and "patient" are used interchangeably herein and refer to a human or non-human animal who is known to have, or potentially has, a medical condition or disorder, such as, e.g., a cancer.

The term "sequence read" as used herein refers to a nucleotide sequence read from a sample obtained from a subject. Sequence reads can be obtained through various methods known in the art.

The term "circulating tumor DNA" or "ctDNA" refers to nucleic acid fragments that originate from tumor cells or other types of cancer cells, which may be released into a subject's bloodstream as a result of biological processes, such as apoptosis or necrosis of dying cells, or may be actively released by viable tumor cells.

DETAILED DESCRIPTION OF THE INVENTION

Aspects of the invention include methods for preparing a sequencing library from a DNA-containing test sample. In one aspect, the present invention is directed to methods for rescuing one or more partially ligated DNA fragments to enhance library preparation conversion efficiencies. In other aspects, the methods can be used to improve recovery of duplex sequence information from double-stranded DNA.

FIG. 1 is a schematic illustration showing ligation steps in a known library preparation method. For example, in TRUSEQ® library preparation (Illumina, San Diego, Calif.), sequencing adapters are typically ligated to both ends of fragmented duplex nucleic acid molecules to prepare nucleic acid molecules for sequencing. As shown, for example in FIG. 1, Y-adapters 105 can be ligated to both ends of a dsDNA fragment having a forward strand 115a and a reverse strand 115b. The Y-adapters 105 may include unique sequence tags, primers, one or more primer binding sites and/or a common sequence region (e.g., a common SBS sequence region). The procedure requires four successful ligation events (shown as L1, L2, L3, and L4) to obtain sequenceable DNA fragments for both duplex target strands (i.e., successful ligations at L1 and L2 are required to obtain a sequenceable fragment for the forward strand 115a, and successful ligations at L3 and L4 are required to obtain a sequenceable DNA fragment for the reverse strand 115b). However, as is well known in the art, these required, independent ligation events, are not 100% efficient. Typically, each individual ligation event may have a 70% probability of being successful, or less, which can lead to a loss of DNA sequences information from the test sample.

In one aspect, the present invention is directed to methods for preparing a sequencing library of dsDNA fragments obtained from a test sample. For example, in some embodiments, a method can be used to prepare a DNA sequencing library from a cell-free nucleic acid (cfNA) sample (e.g., cfDNA and/or cfRNA). In one embodiment, the methods of the present invention can be used as one step in a method for preparing a sequencing library from a combined RNA and DNA cell-free nucleic acid sample. For example, as disclosed in U.S. application Ser. No. 15/638,220, entitled, "Differential tagging of RNA for preparation of a cell-free DNA/RNA sequencing library", which was filed Jun. 29, 2017, and which is incorporated herein by reference.

In another aspect, the present invention is directed to methods for rescuing one or more partially ligated DNA fragments to enhance library preparation conversion efficiencies. As discussed above, at least two successful ligation events on the same strand are required to generate a sequenceable nucleic acid. In accordance with this aspect of the present invention, the methods disclosed herein may include a step for extending the unligated, or free 3'-ends of a dsDNA fragment using a DNA polymerase. For example, a DNA polymerase can be used to synthesize, from the free 3'-ends (i.e., unligated ends) of the dsDNA fragment, a nucleic acid sequence complementary to the ligated strand of the dsDNA adapter.

In still another aspect, the present invention is directed to obtaining duplex DNA sequencing information from a test sample. In one embodiment, the methods of the present invention can be carried out to improve recovery of both the forward strand (i.e., sense strand) and reverse strand (i.e., anti-sense strand) of DNA fragments obtained from a test sample. For example, as is well-known in the art, sequence information from both the forward and reverse strands of a dsDNA fragment can be identified and used to identify errors introduced from amplification, library preparation, enrichment, and/or sequencing. Unique molecular identifiers (UMIs) can be used to uniquely tag, and subsequently identify duplex strands originating from the same dsDNA fragments. Accordingly, UMIs can be used to reduce amplification bias, which is the asymmetric amplification of different targets due to differences in nucleic acid composition (e.g., high GC content), and/or to identify, and correct for, nucleic acid mutations that arise during amplification, library preparation, enrichment, and/or sequencing.

In one embodiment, the present invention is directed to a method for preparing a sequencing library from a test sample comprising a plurality of double-strand DNA fragments, the method comprising the steps: (a) obtaining a test sample comprising a plurality of double-stranded DNA (dsDNA) fragments, wherein the dsDNA fragments comprise a forward strand and a reverse strand; (b) ligating double-strand DNA adapters to both ends of the purified dsDNA fragments; (c) extending unligated 3'-ends of the dsDNA fragments with a DNA polymerase to create dsDNA fragment-adapter templates to prepare a sequencing library. Optionally, the dsDNA molecules can be purified, and optionally fragmented, from a test sample prior to ligation step (b).

Figure 2:
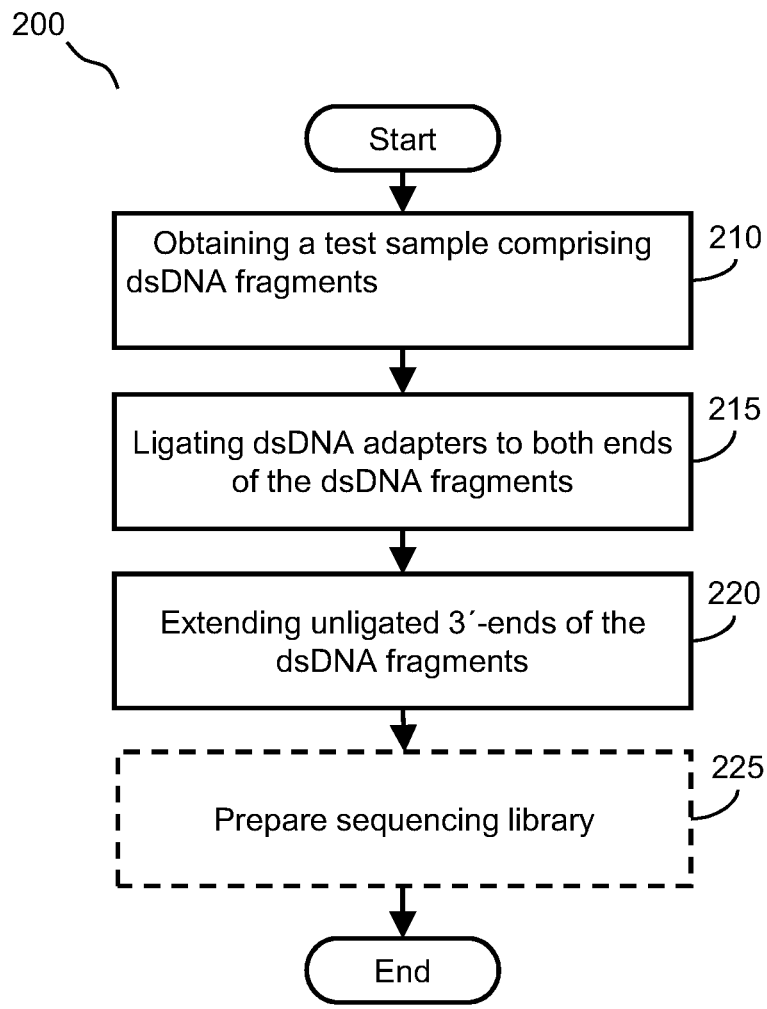
FIG. 2 is a flow diagram illustrating a method for preparing a dsDNA sequencing library from a test sample in accordance with one embodiment of the present invention.

FIG. 2 is a flow diagram illustrating a method for preparing a dsDNA sequencing library from a test sample in accordance with one embodiment of the present invention. In step 210, a DNA-containing test sample is obtained, and optionally double stranded DNA (dsDNA) fragments are purified from the test sample. In general, any known method in the art can be used for purifying dsDNA fragments from the test sample. As described further herein, test samples in accordance with embodiments of the invention may be selected from the group consisting of blood, plasma, serum, urine, fecal, and saliva samples. Alternatively, the biological sample may comprise a sample selected from the group consisting of whole blood, a blood fraction, a tissue biopsy, pleural fluid, pericardial fluid, cerebral spinal fluid, and peritoneal fluid. In one embodiment, the dsDNA fragments comprise cell-free dsDNA. In another embodiment, the dsDNA sequences may be fragmented after purification of the dsDNA fragments from the test sample.

In step 215, dsDNA adapters are ligated to both ends of the dsDNA fragments obtained in step 210. In accordance with this step, dsDNA adapters are added to a reaction mixture comprising the dsDNA fragments, and are ligated to both ends of the dsDNA fragments using a DNA ligase. In general, any known DNA ligase may be used in this ligation step. In one embodiment, T4 DNA ligase is used. Optionally, in one embodiment, the dsDNA fragments are end-repaired and A-tailed at the 3'-ends prior to ligation of the adapters to both ends of the dsDNA fragments. The A-tailed 3'-ends may include one or more adenine bases. In accordance with this optional embodiment, the dsDNA adapters may include one or more thymine (T) bases on the 3'-end to ensure proper alignment of the adapter to the dsDNA fragment prior to ligation. The adapters may include one or more binding sites for the binding of universal primers, amplification primers, or sequencing primers. For example, in one embodiment, the adapters may include one or more complementary sequence regions that allow for the annealing of one or more primer sequences for use in subsequent, or downstream, amplification or sequencing steps.

In one embodiment, the dsDNA adapters may include a unique sequence tag (e.g., a barcode or UMI). Unique sequence tags in accordance with the present invention can serve many functions. Unique sequence tags can include molecular barcode sequences, unique molecular identifier (UMI) sequences, or index sequences. In one embodiment, unique sequence tags (e.g., barcode or index sequences) can be used to identify individual DNA sequences originating from a common test sample such as a common sample, tissue, patient, or individual. In another embodiment, the unique sequence tag is a unique molecular identifier (UMI), and can be used to identify a unique DNA sequences from a test sample (e.g., from mixed cfDNA sample). In still another embodiment, the UMI sequence or tag can be used to reduce errors introduced in subsequent steps of amplification, library preparation, and sequencing. For example, the UMI can be used to reduce amplification bias, which is the asymmetric amplification of different targets due to differences in nucleic acid composition (e.g., high GC content). The unique sequence tags (UMIs) may also be used to identify, and correct for, nucleic acid mutations that arise during amplification, library preparation, or sequencing (i.e., systematic errors). In some embodiments, the unique sequence tags (e.g., barcodes or index sequences) can be used for multiplex sequencing. The unique sequence tag can range in length from about 2 nucleotides (nt) to about 30 nt, from about 3 nt to about 20 nt, or from about 4 nt to about 15 nt.

In step 220, unligated, or free 3'-ends of the dsDNA fragments (i.e., at sites where ligation of the adapter was not successful) can be extended with a DNA polymerase to form a dsDNA fragment-adapter template where both dsDNA adapters have been successfully added, or covalently linked, to the dsDNA fragments. For example, a complementary strand to the ligated strand of the dsDNA adapter can be synthesized from the unligated, or free 3'-end of the dsDNA fragment by a DNA polymerase using the ligated strand as a template and a reaction mixture comprising deoxyribonucleotide triphosphates (i.e., dNTPs). As previously described, four successful ligation events are required to obtain sequenceable fragments for both the forward and reverse strands of a duplex DNA fragment. However, as one of skill in the art would readily recognize, these individual ligations events are not 100% efficient and sequence information from the test sample can be lost. As such, in accordance with step 220, one or more unligated 3'-ends (or free 3'-ends) of the dsDNA fragments can be extended using a DNA polymerase to complete the dsDNA fragment-adapter template. In general, any DNA polymerase can be used in the step. In one embodiment, the DNA polymerase is a DNA polymerase with strand displacement activity. For example, the DNA polymerase can be *Bacillus stearothermophilus* DNA polymerase (Bst Pol) (available from Clontech) or can be phi29 DNA polymerase (available from New England BioLabs, Inc.).

In some embodiments, the subject methods facilitate improved recovery of sequencable, fully ligated dsDNA fragment-adapter constructs. As noted above, obtaining fully sequenceable duplex DNA (i.e., recovery of sequenceable forward and reverse strands of a double-stranded DNA molecule) requires four successful ligation events. If a single ligation event fails during library preparation, one strand of the duplexed library fragment will not be amplified and a non-duplexed read will be observed during subsequent sequence analysis. Also, as noted above, in conventional library preparation methods, each individual ligation event may have a 70% probability of being successful, or less, which can lead to a loss of DNA sequence information from the test sample. One unsuccessful ligation event can lead to a loss of 50% of the sequencable fragments (i.e., loss of one strand of the duplex DNA molecule) and two unsuccessful ligation events can lead to a loss of the entire dsDNA molecule after subsequent sequencing. However, methods in accordance with embodiments of the invention improve the recovery of duplex DNA molecules from a test sample. For example, in some embodiments, the subject methods result in recovery of more than about 50%, such as more than about 55%, such as more than about 60%, such as more than about 65%, such as more than about 70%, such as more than about 75%, such as more than about 80%, such as more than about 85%, such as more than about 90%, such as more than about 95%, or such as more than about 99% of double-strand DNA molecules from an original test sample after sequencing. In other embodiments, the subject methods result in successful addition of adapters to both ends of more than about 50%, such as more than about 55%, such as more than about 60%, such as more than about 65%, such as more than about 70%, such as more than about 75%, such as more than about 80%, such as more than about 85%, such as more than about 90%, such as more than about 95%, or such as more than about 99% of double-strand DNA molecules present in an original test sample.

Optionally, in step 225, a sequencing library is prepared from the dsDNA fragment-adapter templates obtained from step 220. For example, in one embodiment, a set of ssDNA oligonucleotides (e.g., PCR primers), can be annealed to the dsDNA fragment-adapter templates and used for PCR amplification of the dsDNA fragment-adapter templates to complete library preparation. As is well known in the art, PCR amplification may use a DNA polymerase and a reaction mixture containing one or more primers and/or a mixture of deoxyribonucleotide triphosphates (i.e., dNTPs) for amplification of DNA. In some embodiments, the ssDNA oligonucleotides utilized in the practice of this invention may include a universal primer and/or one or more sequencing oligonucleotides for use in subsequent cluster generation and/or sequencing (e.g., known P5 and P7 sequences for used in sequencing by synthesis (SBS) (Illumina, San Diego, Calif.)). In another embodiment, the ssDNA oligonucleotides can be annealed to a complementary sequence (e.g., a common sequencing by synthesis (SBS) sequence (CGCTCTTCCGATCT)) contained in the dsDNA adapters added in steps 215 and 220, and the sequencing adapters extended to complete library preparation. In some embodiment, a fragmentation step may be used prior to preparation of a sequencing library (i.e., prior to step 225 of method 200) to facilitate subsequent sequencing processes (e.g., cluster amplification).

In certain embodiments, aspects of the subject methods further comprise sequencing at least a portion of a DNA sequencing library to obtain sequencing data or sequence reads (not shown). In general, any method known in the art can be used to obtain sequence data or sequence reads from the DNA sequencing library. For example, in one embodiment, sequencing data or sequence reads can be acquired using next generation sequencing (NGS). Next-generation sequencing methods include, for example, sequencing by synthesis technology (Illumina), pyrosequencing (454), ion semiconductor technology (Ion Torrent sequencing), single-molecule real-time sequencing (Pacific Biosciences), sequencing by ligation (SOLiD sequencing), and nanopore sequencing (Oxford Nanopore Technologies). In certain embodiments, the sequencing comprises whole genome sequencing (or shotgun sequencing) of the cfDNA library to provide sequence data or sequencing reads representative of a whole genome. In other embodiments, the sequencing comprises targeted sequencing of the cfDNA library. For example, the sequencing library can be enriched for specific target sequences (e.g., using a plurality of hybridization probes to pull down cfDNA fragments known to be, or suspected of being, indicative of cancer) and the targeted sequences sequenced. Sequencing and bioinformatics methodologies are described further herein.

In some embodiments, one or more steps of a method may be carried out in a single reaction step. For example, steps (b) through (c) may be carried out in a single reaction tube utilizing a reaction mixture comprising a first set of dsDNA adapters, a ligase, a polymerase (optionally having strand-displacement activity), a terminal deoxynucleotidyl transferase, and a second set of ssDNA adapters (e.g., amplification primers).

In another embodiment, aspects of the invention are directed to methods for preparing a sequencing library from a test sample comprising DNA, the methods comprising the steps: (a) obtaining a test sample comprising a plurality of double-stranded DNA (dsDNA) fragments, the dsDNA fragments comprising a forward strand and a reverse strand; (b) adding double-stranded adapters to the purified dsDNA sample and ligating the double-strand adapters to both ends of the dsDNA fragments; (c) extending unligated 3'-ends of the dsDNA fragments with a DNA polymerase to create dsDNA fragment-adapter templates, wherein the polymerase further comprises strand displacement activity; (d) adding a poly-adenine tail to the 3'-ends of the dsDNA fragment-adapter templates; (e) adding a set of ssDNA oligonucleotides (or primers) and hybridizing the ssDNA adapters to the dsDNA fragment-adapter templates; and (f) extending the set of ssDNA oligonucleotides to create a dsDNA sequencing library. Optionally, the dsDNA molecules can be purified, and optionally fragmented, from test sample prior to ligation step (b).

Figure 3:
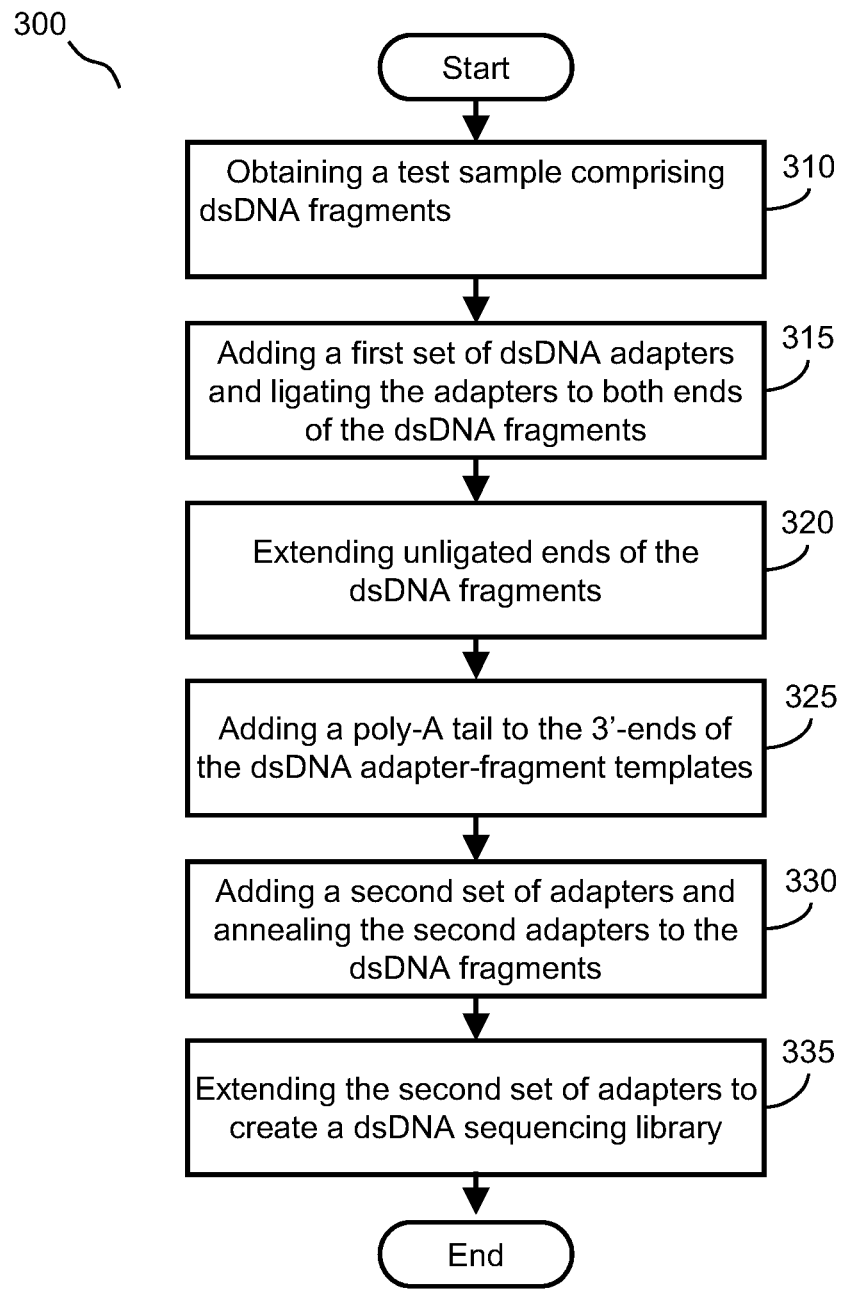
FIG. 3 is a flow diagram illustrating a method for preparing a dsDNA sequencing library from a test sample in accordance with another embodiment of the present invention.

FIG. 3 is a flow diagram illustrating a method for preparing a dsDNA sequencing library from a test sample in accordance with another embodiment of the present invention. As shown, method 200 may include, but is not limited to, the following steps.

In step 310, a DNA-containing test sample is obtained and double stranded DNA (dsDNA) fragments are optionally purified from the test sample. With reference to FIG. 2, as noted above, the test sample may be a sample selected from the group consisting of blood, plasma, serum, urine, fecal, and saliva samples. Alternatively, the test sample may comprise a sample selected from the group consisting of whole blood, a blood fraction, a tissue biopsy, pleural fluid, pericardial fluid, cerebral spinal fluid, and peritoneal fluid. In one embodiment, the dsDNA fragments comprise cell-free dsDNA. Also, as noted above, in general, any known method in the art can be used for purifying dsDNA fragments from the test sample. In another embodiment, the dsDNA sequences may be fragmented after purification of the dsDNA fragments from the test sample.

In step 315, double-strand DNA (dsDNA) adapters are added to a reaction mixture comprising the dsDNA fragments obtained in step 310, and are ligated to both ends of the dsDNA fragments. In accordance with this step, dsDNA adapters are added to the dsDNA sample and ligated to the dsDNA fragments using a DNA ligase. In general, any known DNA ligase may be used in this ligation step. In one embodiment, the adapters may include one or more binding sites for the binding of universal primers, amplification primers, or sequencing primers. For example, in one embodiment, the adapters may include one or more complementary sequence regions that allow for the annealing of one or more primer sequences for use in subsequent, or downstream, amplification or sequencing steps. As noted above, optionally, the dsDNA fragments are end-repaired and A-tailed at the 3'-ends prior to ligation of the adapters to both ends of the dsDNA fragments. The A-tailed 3'-ends may include one or more adenine bases. In accordance with this optional embodiment, the dsDNA adapters may include one or more thymine (T) bases on the 3'-end to ensure proper alignment of the adapter to the dsDNA fragment prior to ligation. In another embodiment, as described in more detail above, the dsDNA adapters may include a unique sequence tag (e.g., a barcode, index sequence, or UMI).

In step 320, one or more unligated 3'-ends (i.e., free 3'-ends) of the dsDNA fragments can be extended using a DNA polymerase to complete the dsDNA fragment-adapter template. As previously described, four successful ligation events are required to obtain sequenceable fragments for both the forward and reverse strands of a duplex DNA fragment. However, as one of skill in the art would readily recognize, these individual ligations events are not 100% efficient and sequence information from the test sample can be lost. To recover sequenceable dsDNA fragments, unligated, or free 3'-ends of the dsDNA fragments (i.e., at sites where ligation of the adapter was not successful) can be extended with a DNA polymerase to form a dsDNA fragment-adapter template where both dsDNA adapters have been successfully added, or covalently linked, to the dsDNA fragments. For example, in one embodiment, a strand complementary to the ligated strand of the dsDNA adapter can be synthesized from the unligated, or free 3'-end of the dsDNA fragment by a DNA polymerase using the ligated strand as a template and a reaction mixture comprising deoxyribonucleotide triphosphates (i.e., dNTPs). In general, any DNA polymerase having strand-displacement activity can be used in the step. In one embodiment, the DNA polymerase is a DNA polymerase with strand displacement activity. For example, the DNA polymerase can be *Bacillus stearothermophilus* DNA polymerase (Bst Pol) (available from Clontech) or can be phi29 DNA polymerase (available from New England BioLabs, Inc.).

Methods in accordance with embodiments of the invention improve recovery of sequencable, fully ligated dsDNA adapter-fragment constructs. As noted above, obtaining fully sequenceable duplex DNA (i.e., recovery of sequenceable forward and reverse strands of a double-stranded DNA molecule) requires four successful ligation events. If a single ligation event fails during library preparation, one strand of the duplexed library fragment will not be amplified and a non-duplexed read will be observed during subsequent sequence analysis. Also, as noted above, in conventional library preparation methods, each individual ligation event may have a 70% probability of being successful, or less, which can lead to a loss of DNA sequence information from the test sample. One unsuccessful ligation event can lead to a loss of 50% of the sequencable fragments (i.e., loss of one strand of the duplex DNA molecule) and two unsuccessful ligation events can lead to a loss of the entire dsDNA molecule after subsequent sequencing. However, methods in accordance with embodiments of the invention improve the recovery of duplex DNA molecules from a test sample. In one embodiment, the subject methods result in recovery of more than about 50%, such as more than about 55%, such as more than about 60%, such as more than about 65%, such as more than about 70%, such as more than about 75%, such as more than about 80%, such as more than about 85%, such as more than about 90%, such as more than about 95%, or such as more than about 99% of double-strand DNA molecules from the original test sample after sequencing. In another embodiment, the subject methods result in successful addition of adapters to both ends of more than about 50%, such as more than about 55%, such as more than about 60%, such as more than about 65%, such as more than about 70%, such as more than about 75%, such as more than about 80%, such as more than about 85%, such as more than about 90%, such as more than about 95%, or such as more than about 99% of double-strand DNA molecules present in the original test sample.

In step 325, a poly-adenine (poly-A) tail is added to the 3'-ends of the dsDNA adapter-fragment templates. For example, a poly-A tail can be added using a terminal deoxynucleotidyl transferase (TdT) to the 3'-ends of both the forward and reverse strands of the dsDNA adapter-fragment templates creating poly-A tailed dsDNA fragment-adapter templates. The poly-A tail may comprise from about 2 to about 40 adenine bases, from about 3 to about 30, or from about 5 to about 20 adenine bases.

In step 330, a set of ssDNA oligonucleotides (or primers) are added to the reaction mixture and annealed to the poly-A tailed dsDNA fragment-adapter templates obtained in step 325. For example, in one embodiment, a set of ssDNA oligonucleotides (e.g., PCR primers), can be annealed to the dsDNA fragment-adapter templates and used for PCR amplification to complete library preparation. As is well known in the art, PCR amplification may use a DNA polymerase and a reaction mixture containing one or more primers and/or a mixture of deoxyribonucleotide triphosphates (i.e., dNTPs) for amplification of DNA. In some embodiments, the ssDNA adapters utilized in the practice of this invention may include a universal primer and/or one or more sequencing oligonucleotides for use in subsequent cluster generation and/or sequencing (e.g., known P5 and P7 sequences for used in sequencing by synthesis (SBS) (Illumina, San Diego, Calif.)). In another embodiment, the ssDNA oligonucleotides can be annealed to a complementary sequence (e.g., a common sequencing by synthesis (SBS) sequence (CGCTCTTCCGATCT)) contained in the dsDNA adapters added in steps 315 and 320, and the sequencing adapters extended to complete library preparation.

In step 335, the ssDNA oligonucleotides annealed to the dsDNA fragment-adapter templates in step 330 are extended to create a dsDNA sequencing library. For example, in one embodiment, the ssDNA oligonucleotides comprise PCR primers that can be annealed to the dsDNA adapters and/or poly-A tails (added in steps 315 and 325, respectively) and used for PCR amplification of the construct. In another embodiment, the ssDNA oligonucleotides may comprise one or more sequencing oligonucleotides for use in subsequent cluster generation and/or sequencing (e.g., known P5 and P7 sequences for used in sequencing by synthesis (SBS) (Illumina, San Diego, Calif.)).

In some embodiments, one or more steps of the method may be carried out in a single reaction step. For example, steps (b) through (g) may be carried out in a single reaction tube utilizing a reaction mixture comprising a first set of dsDNA adapters, a ligase, a polymerase (optionally having strand-displacement activity), a terminal deoxynucleotidyl transferase, and a second set of ssDNA oligonucleotides (e.g., amplification primers). In other embodiments, a fragmentation step may be used prior to preparation of a sequencing library (i.e., prior to step 230 of method 200) to facilitate subsequent sequencing processes (e.g., cluster amplification).

In some embodiments, the method further comprises sequencing at least a portion of the DNA sequencing library to obtain sequencing data or sequence reads (not shown). In general, any method known in the art can be used to obtain sequence data or sequence reads from the DNA sequencing library. For example, in one embodiment, sequencing data or sequence reads can be acquired using next generation sequencing (NGS). Next-generation sequencing methods include, for example, sequencing by synthesis technology (Illumina), pyrosequencing (454), ion semiconductor technology (Ion Torrent sequencing), single-molecule real-time sequencing (Pacific Biosciences), sequencing by ligation (SOLiD sequencing), and nanopore sequencing (Oxford Nanopore Technologies). In certain embodiments, the sequencing comprises whole genome sequencing (or shotgun sequencing) of the cfDNA library to provide sequence data or sequencing reads representing a whole genome. In other embodiments, the sequencing comprises targeted sequencing of the cfDNA library. For example, the sequencing library can be enriched for specific target sequences (e.g., using a plurality of hybridization probes to pull down cfDNA fragments known to be, or suspected of being, indicative of cancer) and the targeted sequences sequenced.

Figure 4:
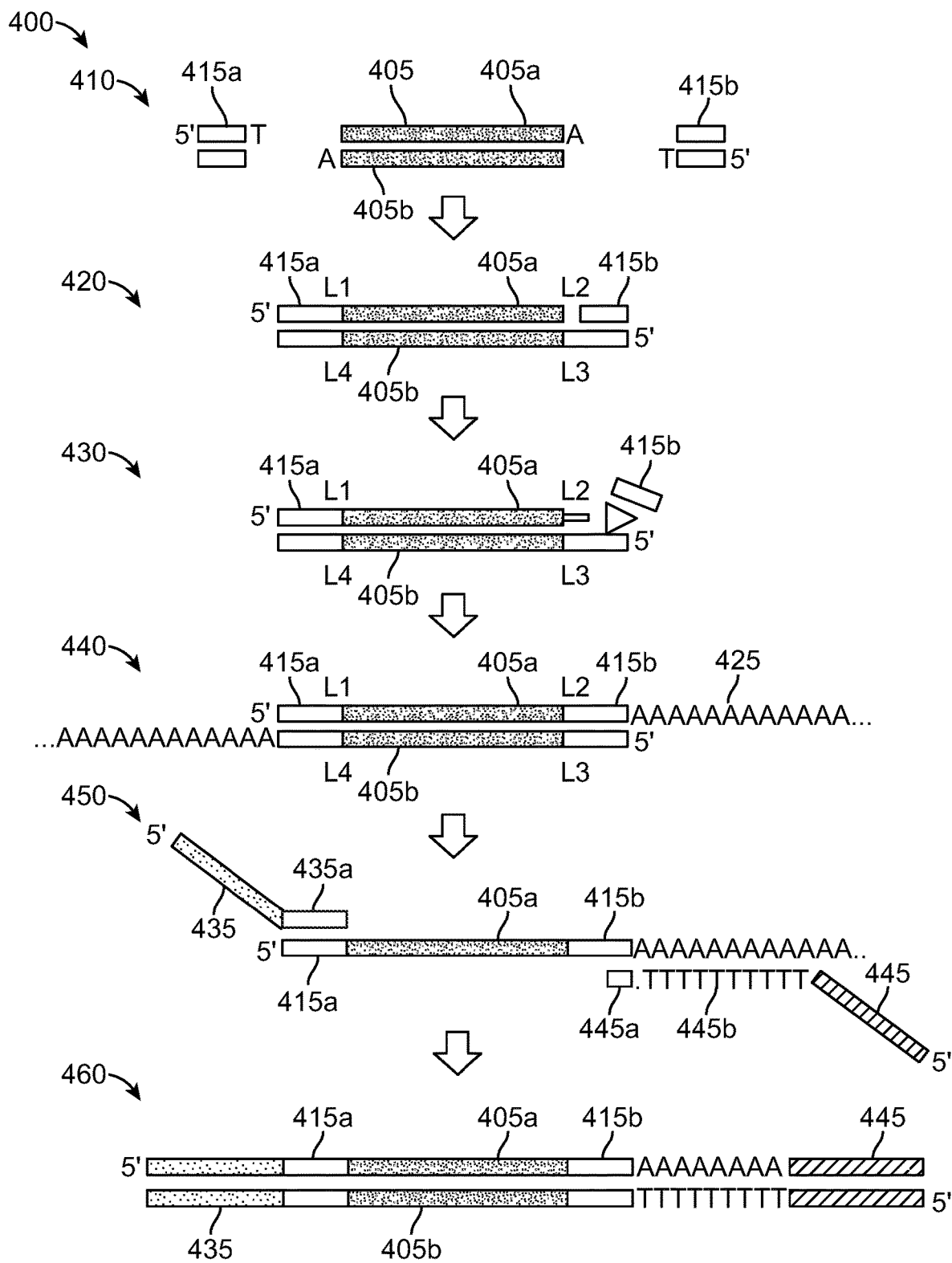
FIG. 4 shows pictorially the steps of a method for preparing a dsDNA sequencing library from a test sample in accordance with the embodiment shown in FIG. 3.

FIG. 4 shows pictorially the steps of a method 400 for preparing a dsDNA sequencing library from a test sample in accordance with the embodiment shown in FIG. 3. As shown, method 400 may include, but is not limited to, the following steps.

The method 400 illustrated in FIG. 4 starts with a purified DNA sample that has been purified from the test sample (not shown). The purified DNA sample comprises a plurality of dsDNA fragments 405, having a forward (i.e., sense) strand 405a and a reverse (i.e., antisense) strand 405b. In general, the test sample can be any known nucleic acid comprising biological sample. Exemplary test samples are detailed above. In one embodiment, the dsDNA fragments comprise cell-free dsDNA. Also, as noted above, in general, any known method in the art can be used for purifying dsDNA fragments from the test sample. In another embodiment, the dsDNA sequences may be fragmented after purification of the dsDNA fragments from the test sample.

In step 410, double-strand DNA (dsDNA) adapters 415a, 415b are added to a reaction mixture comprising the purified dsDNA fragments, and are ligated to both ends of the purified dsDNA fragments 405. In accordance with this step, dsDNA adapters 415a, 415b are added to the purified dsDNA sample and ligated to the dsDNA fragments using a DNA ligase. In general, any known DNA ligase may be used in this ligation step. In one embodiment, the adapters may include one or more binding sites for the binding of universal primers, amplification primers, or sequencing primers. As shown in FIG. 4, four ligation events (L1, L2, L3, and L4) are required to form the completed dsDNA fragment-adapter templates. However, as shown in FIG. 4, one ligation even (L2) has not been successful, resulting in an unligated, or free 3'-end on the forward strand 405a.

In one embodiment, the adapters 415a, 415b may include one or more complementary sequence regions (not shown) that allow for the annealing of one or more primer sequences for use in subsequent, or downstream, amplification or sequencing steps. As shown in FIG. 4, the dsDNA fragments 405 are A-tailed at the 3'-ends with a single adenine base and the adapters 415a, 415b include a single free 5'-end thymine base. The free 5'-thymine (T) base allows for proper alignment with the 3'-adenine on the dsDNA fragments 405 to ensure proper alignment of the adapter to the dsDNA fragment prior to ligation. In another embodiment, as described in more detail above, the dsDNA adapters may include a unique sequence tag (e.g., a barcode, index sequence, or UMI), as described elsewhere in this application.

In step 430, one or more unligated 3'-ends (i.e., free 3'-ends) of the dsDNA fragments 405 can be extended using a DNA polymerase to complete the dsDNA fragment-adapter template. For example, as shown in FIG. 4, the free 3'-end of the forward (i.e., sense) strand 405a remains unligated to the 5'-end dsDNA adapter 415b. Because the adapter is not ligated to the 3'-end of the forward strand 405a dsDNA fragment 405, the forward strand 405a cannot be sequenced, and any sequence data contained therein will be lost. However, in accordance with this step, the forward strand 405a can be recovered by utilizing the complementary strand of the dsDNA adapter 415b as a template for extension of the 3'-end of the dsDNA fragment 405a using a DNA polymerase. As shown, this DNA polymerase extension of the dsDNA fragment 405 results in the formation of a complete dsDNA fragment-adapter template and recover of a sequenceable forward strand 405a. In general, any DNA polymerase having strand-displacement activity can be used in the step. In one embodiment, the DNA polymerase is a DNA polymerase with strand displacement activity. For example, the DNA polymerase can be *Bacillus stearothermophilus* DNA polymerase (Bst Pol) (available from Clontech) or can be phi29 DNA polymerase (available from New England BioLabs, Inc.).

In step 440, a poly-adenine (poly-A) tail 425 is added to the 3'-ends of the dsDNA adapter-fragment templates using a terminal deoxynucleotidyl transferase (TdT). As shown, a poly-A tail is added to 3'-ends of both the forward and reverse strands of the dsDNA adapter-fragment templates creating poly-A tailed dsDNA fragment-adapter templates. The poly-A tails may comprise from about 2 to about 40 adenine bases, from about 3 to about 30, or from about 5 to about 20 adenine bases. As shown, in one embodiment, the poly-A tail comprises about 12 adenine bases.

In step 450, ssDNA oligonucleotides 435, 445 are added to the reaction mixture and annealed to the dsDNA fragment-adapter templates. As shown, a first ssDNA oligonucleotide 435 is annealed to the 5'-end of the forward strand 405a of the dsDNA fragment-adapter template 405a and a second ssDNA oligonucleotide 445 is annealed to the poly-A tail added to the dsDNA fragment-adapter template in step 440. In one embodiment, the first ssDNA oligonucleotide 435, includes a sequence region 435a which is the same as a sequence region (e.g., an SBS common sequence) in the 5'-end of the dsDNA adapter 415a, allowing the first ssDNA adapter 435 to anneal to specific location on the dsDNA fragment-adapter template. Similarly, the second ssDNA oligonucleotide 445 includes a sequence region 445a complementary to a sequence region (e.g., an SBS common sequence) in the 3'-end of the dsDNA adapter, and a poly-thymine (poly-T) tail complementary to the poly-A tail, allowing the second ssDNA adapter 445 to anneal to a specific location on the dsDNA fragment-adapter template.

In step 460, the ssDNA oligonucleotides 435, 445 are extended to create a dsDNA sequencing library. For example, as shown in FIG. 4, the ssDNA oligonucleotides 435, 445 comprise PCR primers that can be annealed to the dsDNA adapters and/or poly-A tails (as shown in step 450) and used for PCR amplification of the construct. In another embodiment, the ssDNA oligonucleotides may comprise one or more sequencing oligonucleotides for use in subsequent cluster generation and/or sequencing (e.g., known P5 and P7 sequences for used in sequencing by synthesis (SBS) (Illumina, San Diego, Calif.)).

Sequencing and Bioinformatics

As reviewed above, aspects of the invention include sequencing of nucleic acid molecules to generate a plurality of sequence reads, compilation of a plurality of sequence reads into a sequencing library, and bioinformatic manipulation of the sequence reads and/or sequencing library to determine sequence information from a test sample (e.g., a biological sample). In some embodiments, one or more aspects of the subject methods are conducted using a suitably-programmed computer system, as described further herein.

In certain embodiments, a sample is collected from a subject, followed by enrichment for genetic regions or genetic fragments of interest. For example, in some embodiments, a sample can be enriched by hybridization to a nucleotide array comprising cancer-related genes or gene fragments of interest. In some embodiments, a sample can be enriched for genes of interest (e.g., cancer-associated genes) using other methods known in the art, such as hybrid capture. See, e.g., Lapidus (U.S. Pat. No. 7,666,593), the contents of which is incorporated by reference herein in its entirety. In one hybrid capture method, a solution-based hybridization method is used that includes the use of biotinylated oligonucleotides and streptavidin coated magnetic beads. See, e.g., Duncavage et al., J Mol Diagn. 13(3): 325-333 (2011); and Newman et al., Nat Med. 20(5): 548-554 (2014). Isolation of nucleic acid from a sample in accordance with the methods of the invention can be done according to any method known in the art.

Sequencing may be by any method or combination of methods known in the art. For example, known DNA sequencing techniques include, but are not limited to, classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, Polony sequencing, and SOLiD sequencing. Sequencing of separated molecules has more recently been demonstrated by sequential or single extension reactions using polymerases or ligases as well as by single or sequential differential hybridizations with libraries of probes.

One conventional method to perform sequencing is by chain termination and gel separation, as described by Sanger et al., Proc Natl. Acad. Sci. USA, 74(12): 5463 67 (1977), the contents of which are incorporated by reference herein in their entirety. Another conventional sequencing method involves chemical degradation of nucleic acid fragments. See, Maxam et al., Proc. Natl. Acad. Sci., 74: 560 564 (1977), the contents of which are incorporated by reference herein in their entirety. Methods have also been developed based upon sequencing by hybridization. See, e.g., Harris et al., (U.S. patent application number 2009/0156412), the contents of which are incorporated by reference herein in their entirety.

A sequencing technique that can be used in the methods of the provided invention includes, for example, Helicos True Single Molecule Sequencing (tSMS) (Harris T. D. et al. (2008) Science 320:106-109), the contents of which are incorporated by reference herein in their entirety. Further description of tSMS is shown, for example, in Lapidus et al. (U.S. Pat. No. 7,169,560), the contents of which are incorporated by reference herein in their entirety, Lapidus et al. (U.S. patent application publication number 2009/0191565, the contents of which are incorporated by reference herein in their entirety), Quake et al. (U.S. Pat. No. 6,818,395, the contents of which are incorporated by reference herein in their entirety), Harris (U.S. Pat. No. 7,282,337, the contents of which are incorporated by reference herein in their entirety), Quake et al. (U.S. patent application publication number 2002/0164629, the contents of which are incorporated by reference herein in their entirety), and Braslaysky, et al., PNAS (USA), 100: 3960-3964 (2003), the contents of which are incorporated by reference herein in their entirety.

Another example of a DNA sequencing technique that can be used in the methods of the provided invention is 454 sequencing (Roche) (Margulies, M et al. 2005, Nature, 437, 376-380, the contents of which are incorporated by reference herein in their entirety). Another example of a DNA sequencing technique that can be used in the methods of the provided invention is SOLiD technology (Applied Biosystems). Another example of a DNA sequencing technique that can be used in the methods of the provided invention is Ion Torrent sequencing (U.S. patent application publication numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the contents of each of which are incorporated by reference herein in their entirety).

In some embodiments, the sequencing technology is Illumina sequencing. Illumina sequencing is based on the amplification of DNA on a solid surface using fold-back PCR and anchored primers. Genomic DNA can be fragmented, or in the case of cfDNA, fragmentation is not needed due to the already short fragments. Adapters are ligated to the 5'- and 3'-ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. Yet another example of a sequencing technique that can be used in the methods of the provided invention is nanopore sequencing (Soni G V and Meller A. (2007) Clin Chem 53: 1996-2001, the contents of which are incorporated by reference herein in their entirety). Another example of a sequencing technique that can be used in the methods of the provided invention involves using a chemical-sensitive field effect transistor (chemFET) array to sequence DNA (for example, as described in US Patent Application Publication No. 20090026082, the contents of which are incorporated by reference herein in their entirety). Another example of a sequencing technique that can be used in the methods of the provided invention involves using an electron microscope (Moudrianakis E. N. and Beer M. Proc Natl Acad Sci USA. 1965 March; 53:564-71, the contents of which are incorporated by reference herein in their entirety).

If the nucleic acid from the sample is degraded or only a minimal amount of nucleic acid can be obtained from the sample, PCR can be performed on the nucleic acid in order to obtain a sufficient amount of nucleic acid for sequencing (See, e.g., Mullis et al. U.S. Pat. No. 4,683,195, the contents of which are incorporated by reference herein in its entirety).

Biological Samples

Aspects of the invention involve obtaining a test sample, e.g., a biological sample, such as a tissue and/or body fluid sample, from a subject for purposes of analyzing a plurality of nucleic acids (e.g., a plurality of DNA and/or RNA molecules) therein. Samples in accordance with embodiments of the invention can be collected in any clinically-acceptable manner. Any test sample suspected of containing a plurality of nucleic acids can be used in conjunction with the methods of the present invention. In some embodiments, a test sample can comprise a tissue, a body fluid, or a combination thereof. In some embodiments, a biological sample is collected from a healthy subject. In some embodiments, a biological sample is collected from a subject who is known to have a particular disease or disorder (e.g., a particular cancer or tumor). In some embodiments, a biological sample is collected from a subject who is suspected of having a particular disease or disorder.

As used herein, the term "tissue" refers to a mass of connected cells and/or extracellular matrix material(s). Non-limiting examples of tissues that are commonly used in conjunction with the present methods include skin, hair, finger nails, endometrial tissue, nasal passage tissue, central nervous system (CNS) tissue, neural tissue, eye tissue, liver tissue, kidney tissue, placental tissue, mammary gland tissue, gastrointestinal tissue, musculoskeletal tissue, genitourinary tissue, bone marrow, and the like, derived from, for example, a human or non-human mammal. Tissue samples in accordance with embodiments of the invention can be prepared and provided in the form of any tissue sample types known in the art, such as, for example and without limitation, formalin-fixed paraffin-embedded (FFPE), fresh, and fresh frozen (FF) tissue samples.

As used herein, the term "body fluid" refers to a liquid material derived from a subject, e.g., a human or non-human mammal. Non-limiting examples of body fluids that are commonly used in conjunction with the present methods include mucous, blood, plasma, serum, serum derivatives, synovial fluid, lymphatic fluid, bile, phlegm, saliva, sweat, tears, sputum, amniotic fluid, menstrual fluid, vaginal fluid, semen, urine, cerebrospinal fluid (CSF), such as lumbar or ventricular CSF, gastric fluid, a liquid sample comprising one or more material(s) derived from a nasal, throat, or buccal swab, a liquid sample comprising one or more materials derived from a lavage procedure, such as a peritoneal, gastric, thoracic, or ductal lavage procedure, and the like.

In some embodiments, a test sample can comprise a fine needle aspirate or biopsied tissue. In some embodiments, a test sample can comprise media containing cells or biological material. In some embodiments, a test sample can comprise a blood clot, for example, a blood clot that has been obtained from whole blood after the serum has been removed. In some embodiments, a test sample can comprise stool. In one preferred embodiment, a test sample is drawn whole blood. In one aspect, only a portion of a whole blood sample is used, such as plasma, red blood cells, white blood cells, and platelets. In some embodiments, a test sample is separated into two or more component parts in conjunction with the present methods. For example, in some embodiments, a whole blood sample is separated into plasma, red blood cell, white blood cell, and platelet components.

In some embodiments, a test sample includes a plurality of nucleic acids not only from the subject from which the test sample was taken, but also from one or more other organisms, such as viral DNA/RNA that is present within the subject at the time of sampling.

Nucleic acid can be extracted from a test sample according to any suitable methods known in the art, and the extracted nucleic acid can be utilized in conjunction with the methods described herein. See, e.g., Maniatis, et al., Molecular Cloning: A Laboratory Manual, Cold Spring Harbor, N.Y., pp. 280-281, 1982, the contents of which are incorporated by reference herein in their entirety.

In one preferred embodiment, cell-free nucleic acid (e.g., cell-free DNA (cfDNA) and/or cell-free RNA (cfRNA)) are extracted from a test sample. cfDNA are short base nuclear-derived DNA fragments present in several bodily fluids (e.g. plasma, stool, urine). See, e.g., Mouliere and Rosenfeld, PNAS 112(11): 3178-3179 (March 2015); Jiang et al., PNAS (March 2015); and Mouliere et al., Mol Oncol, 8(5):927-41 (2014). Tumor-derived circulating tumor nucleic acids (e.g., ctDNA and/or ctRNA) constitutes a minority population of cfNAs (i.e., cfDNA and/or cfRNA), in some cases, varying up to about 50%. In some embodiments, ctDNA and/or ctRNA varies depending on tumor stage and tumor type. In some embodiments, ctDNA and/or ctRNA varies from about 0.001% up to about 30%, such as about 0.01% up to about 20%, such as about 0.01% up to about 10%. The covariates of ctDNA and/or ctRNA are not fully understood, but appear to be positively correlated with tumor type, tumor size, and tumor stage. E.g., Bettegowda et al, Sci Trans Med, 2014; Newmann et al, Nat Med, 2014. Despite the challenges associated with the low population of ctDNA/ctRNA in cfNAs, tumor variants have been identified in ctDNA and/or ctRNA across a wide span of cancers. E.g., Bettegowda et al, Sci Trans Med, 2014. Furthermore, analysis of cfDNA and/or cfRNA versus tumor biopsy is less invasive, and methods for analyzing, such as sequencing, enable the identification of sub-clonal heterogeneity. Analysis of cfDNA and/or cfRNA has also been shown to provide for more uniform genome-wide sequencing coverage as compared to tumor tissue biopsies. In some embodiments, a plurality of cfDNA and/or cfRNA are extracted from a sample in a manner that reduces or eliminates co-mingling of cfDNA and genomic DNA. For example, in some embodiments, a sample is processed to isolate a plurality of the cfDNA and/or cfRNA therein in less than about 2 hours, such as less than about 1.5, 1 or 0.5 hours.

A non-limiting example of a procedure for preparing nucleic acid from a blood sample follows. Blood may be collected in 10 mL EDTA tubes (for example, the BD VACUTAINER® family of products from Becton Dickinson, Franklin Lakes, N.J.), or in collection tubes that are adapted for isolation of cfDNA (for example, the CELL FREE DNA BCT® family of products from Streck, Inc., Omaha, Nebr.) can be used to minimize contamination through chemical fixation of nucleated cells, but little contamination from genomic DNA is observed when samples are processed within 2 hours or less, as is the case in some embodiments of the present methods. Beginning with a blood sample, plasma may be extracted by centrifugation, e.g., at 3000 rpm for 10 minutes at room temperature minus brake. Plasma may then be transferred to 1.5 ml tubes in 1 ml aliquots and centrifuged again at 7000 rpm for 10 minutes at room temperature. Supernatants can then be transferred to new 1.5 ml tubes. At this stage, samples can be stored at −80° C. In certain embodiments, samples can be stored at the plasma stage for later processing, as plasma may be more stable than storing extracted cfDNA and/or cfRNA.

Plasma DNA and/or RNA can be extracted using any suitable technique. For example, in some embodiments, plasma DNA and/or RNA can be extracted using one or more commercially available assays, for example, the QIAmp Circulating Nucleic Acid Kit family of products (Qiagen N.V., Venlo Netherlands). In certain embodiments, the following modified elution strategy may be used. DNA and/or RNA may be extracted using, e.g., a QIAmp Circulating Nucleic Acid Kit, following the manufacturer's instructions (maximum amount of plasma allowed per column is 5 mL). If cfDNA and/or cfRNA are being extracted from plasma where the blood was collected in Streck tubes, the reaction time with proteinase K may be doubled from 30 min to 60 min. Preferably, as large a volume as possible should be used (i.e., 5 mL). In various embodiments, a two-step elution may be used to maximize cfDNA and/or cfRNA yield. First, DNA and/or RNA can be eluted using 30 μL of buffer AVE for each column. A minimal amount of buffer necessary to completely cover the membrane can be used in the elution in order to increase cfDNA and/or cfRNA concentration. By decreasing dilution with a small amount of buffer, downstream desiccation of samples can be avoided to prevent melting of double stranded DNA or material loss. Subsequently, about 30 μL of buffer for each column can be eluted. In some embodiments, a second elution may be used to increase DNA and/or RNA yield.

Computer Systems and Devices

Aspects of the invention described herein can be performed using any type of computing device, such as a computer, that includes a processor, e.g., a central processing unit, or any combination of computing devices where each device performs at least part of the process or method. In some embodiments, systems and methods described herein may be performed with a handheld device, e.g., a smart tablet, or a smart phone, or a specialty device produced for the system.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer programs include, by way of example, both general and special purpose microprocessors, and any one or more processors of any kind of digital computer. Generally, a processor will receive instructions and data from a read-only memory or a random access memory, or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including, by way of example, semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through a network by any form or medium of digital data communication, e.g., a communication network. For example, a reference set of data may be stored at a remote location and a computer can communicate across a network to access the reference data set for comparison purposes. In other embodiments, however, a reference data set can be stored locally within the computer, and the computer accesses the reference data set within the CPU for comparison purposes. Examples of communication networks include, but are not limited to, cell networks (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, a data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification (RFID) tags or chips, or any other medium that can be used to store the desired information, and which can be accessed by a computing device.

Functions described herein can be implemented using software, hardware, firmware, hardwiring, or combinations of any of these. Any of the software can be physically located at various positions, including being distributed such that portions of the functions are implemented at different physical locations.

As one skilled in the art would recognize as necessary or best-suited for performance of the methods of the invention, a computer system for implementing some or all of the described inventive methods can include one or more processors (e.g., a central processing unit (CPU) a graphics processing unit (GPU), or both), main memory and static memory, which communicate with each other via a bus.

A processor will generally include a chip, such as a single core or multi-core chip, to provide a central processing unit (CPU). A process may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system. Preferably, each computer includes a non-transitory memory such as a solid state drive, flash drive, disk drive, hard drive, etc.

While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to, one or more solid-state memories (e.g., subscriber identity module (SIM) card, secure digital card (SD card), micro SD card, or solid-state drive (SSD)), optical and magnetic media, and/or any other tangible storage medium or media.

A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Any of the software can be physically located at various positions, including being distributed such that portions of the functions are implemented at different physical locations.

Additionally, systems of the invention can be provided to include reference data. Any suitable genomic data may be stored for use within the system. Examples include, but are not limited to: comprehensive, multi-dimensional maps of the key genomic changes in major types and subtypes of cancer from The Cancer Genome Atlas (TCGA); a catalog of genomic abnormalities from The International Cancer Genome Consortium (ICGC); a catalog of somatic mutations in cancer from COSMIC; the latest builds of the human genome and other popular model organisms; up-to-date reference SNPs from dbSNP; gold standard indels from the 1000 Genomes Project and the Broad Institute; exome capture kit annotations from Illumina, Agilent, Nimblegen, and Ion Torrent; transcript annotations; small test data for experimenting with pipelines (e.g., for new users).

In some embodiments, data is made available within the context of a database included in a system. Any suitable database structure may be used including relational databases, object-oriented databases, and others. In some embodiments, reference data is stored in a relational database such as a "not-only SQL" (NoSQL) database. In certain embodiments, a graph database is included within systems of the invention. It is also to be understood that the term "database" as used herein is not limited to one single database; rather, multiple databases can be included in a system. For example, a database can include two, three, four, five, six, seven, eight, nine, ten, fifteen, twenty, or more individual databases, including any integer of databases therein, in accordance with embodiments of the invention. For example, one database can contain public reference data, a second database can contain test data from a patient, a third database can contain data from healthy individuals, and a fourth database can contain data from sick individuals with a known condition or disorder. It is to be understood that any other configuration of databases with respect to the data contained therein is also contemplated by the methods described herein.

References and citations to other documents, such as patents, patent applications, patent publications, journals, books, papers, web contents, have been made throughout this disclosure. All such documents are hereby incorporated herein by reference in their entirety for all purposes.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof. All references cited throughout the specification are expressly incorporated by reference herein.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

While the present invention has been described with reference to the specific embodiments thereof, it should be understood by those skilled in the art that various changes may be made and equivalents may be substituted without departing from the true spirit and scope of the invention. In addition, many modifications may be made to adapt to a particular situation, material, composition of matter, process, process step or steps, to the objective, spirit and scope of the present invention. All such modifications are intended to be within the scope of the claims appended hereto.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

What is claimed is:

1. A method for preparing a sequencing library from a test sample comprising a plurality of double-stranded DNA fragments, the method comprising:
   (a) obtaining a test sample comprising a plurality of double-stranded DNA (dsDNA) fragments, the dsDNA fragments comprising a forward strand and a reverse strand;
   (b) adding double-stranded adapters to the dsDNA sample and ligating the double-stranded adapters to both ends of the dsDNA fragments;
   (c) extending unligated 3'-ends of the dsDNA fragments with a DNA polymerase to create dsDNA fragment-adapter templates, wherein the polymerase further comprises strand displacement activity;
   (d) adding a poly-adenine tail to the 3'-ends of the dsDNA fragment-adapter templates;
   (e) adding a set of single-stranded DNA (ssDNA) oligonucleotides and hybridizing the ssDNA oligonucleotides to the dsDNA fragment-adapter templates; and
   (f) extending the set of ssDNA oligonucleotides to create a dsDNA sequencing library.

2. The method of claim 1, wherein the dsDNA sequencing library is sequenced to obtain sequence reads.

3. The method of claim 2, wherein the sequence reads are obtained from next-generation sequencing (NGS).

4. The method of claim 2, wherein the sequence reads are obtained from massively parallel sequencing using sequencing-by-synthesis.

5. The method of claim 1, wherein the test sample comprises a plurality of cell-free DNA molecules.

6. The method of 5, wherein the test sample is from a whole blood, a blood fraction, plasma, serum, urine, fecal, saliva, a tissue biopsy, pleural fluid, pericardial fluid, cerebral spinal fluid, or peritoneal fluid test sample.

7. The method of claim 5, wherein the test sample includes nucleic acids originating from healthy cells and from cancer cells.

8. The method of claim 1, wherein the DNA fragments are end-repaired and adenine tailed at the 3'-end prior to ligation in step (b).

9. The method of claim 1, wherein the DNA polymerase used in step (c) is *Bacillus stearothermophilus* DNA polymerase (Bst Pol) or phi29 DNA polymerase.

10. The method of claim 1, wherein the dsDNA adapters comprise a unique molecule tag.

11. The method of claim 10, wherein the dsDNA adapters further comprise a universal primer.

12. The method of claim 1, wherein a terminal deoxynucleotidyl transferase catalyzes the addition of the 3' poly-adenine tail in step (d).

13. The method of claim 1, wherein the set of ssDNA oligonucleotides comprise amplification primers.

14. The method of claim 13, where the set of ssDNA oligonucleotides further comprise an indexing sequence.

15. The method of claim 1, wherein the set of ssDNA oligonucleotides comprise a first ssDNA oligonucleotide and a second ssDNA oligonucleotide, wherein the first and second ssDNA oligonucleotides are complementary to a region on the dsDNA adapters.

16. The method of claim 15, wherein the second ssDNA oligonucleotides further comprise a poly-T region.

17. The method of claim 13, wherein the method further comprises PCR amplification of the dsDNA fragment-adapter templates to create a sequencing library.

* * * * *